(12) United States Patent
Koenig et al.

(10) Patent No.: US 6,610,314 B2
(45) Date of Patent: Aug. 26, 2003

(54) ANTIMICROBIAL FORMULATIONS

(75) Inventors: David W. Koenig, Menasha, WI (US); Lisa M. Kroll, Appleton, WI (US); David R. Otts, Appleton, WI (US); Douglas B. Cole, Hortonville, WI (US); Katherine D. Stahl, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/804,295

(22) Filed: Mar. 12, 2001

(65) Prior Publication Data

US 2002/0169149 A1 Nov. 14, 2002

(51) Int. Cl.⁷ ................................. A01N 25/34
(52) U.S. Cl. ........................ 424/402; 424/404
(58) Field of Search ................... 424/402, 404

(56) References Cited

U.S. PATENT DOCUMENTS

| | | | |
|---|---|---|---|
| 967,688 | A | 8/1910 | Titherly |
| 3,814,096 | A | 6/1974 | Weiss et al. |
| 3,849,241 | A | 11/1974 | Butin et al. |
| 4,100,324 | A | 7/1978 | Anderson et al. |
| 4,112,167 | A | 9/1978 | Dake et al. |
| 4,139,485 | A | 2/1979 | Imokawa et al. |
| 4,369,134 | A | 1/1983 | Deguchi et al. |
| 4,465,613 | A | 8/1984 | Carter |

(List continued on next page.)

FOREIGN PATENT DOCUMENTS

| | | |
|---|---|---|
| CA | 1087956 A | 10/1980 |
| CA | 1334273 C | 2/1995 |
| CA | 2003839 C | 8/1995 |
| CA | 2003842 C | 8/1995 |
| CA | 1337106 C | 9/1995 |
| CA | 2003841 C | 10/1995 |
| EP | 0392665 | 10/1990 |
| EP | 0675076 A2 | 10/1995 |
| WO | WO 00/00026 | 1/2000 |

OTHER PUBLICATIONS

Nikaido et al., Molecular Basis of Bacterial Outer Membrane Permeability, *Microbiological Reviews*, Mar. 1985, pp. 1–32, vol. 49, No. 1, American Society for Microbiology, USA.

Russell, Mechanisms of bacterial resistance to antibacterial agents, *Pharmacy International*, Dec. 1986, pp. 300–308, vol. 7, Elsevier Science Publishers B.V., Amsterdam.

*Primary Examiner*—Thurman K. Page
*Assistant Examiner*—S. Howard
(74) *Attorney, Agent, or Firm*—Senniger, Powers, Leavitt & Roedel

(57) ABSTRACT

Antimicrobial formulations, which may be essentially free of an antimicrobial active, comprising one or more proton donating agents and an alkyl phosphate anionic surfactant comprising a mono alkyl phosphate having the chemical structure:

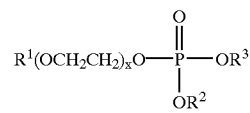

wherein $R^1$ is a saturated or unsaturated straight chain or branched alkyl group having from about 8 to about 22 carbon atoms, x is a number from 0 to about 20, and $R^2$ and $R^3$ are independently selected from hydrogen, an alkali metal, or an alkanol amine, are provided and described herein. The formulations may be incorporated into wet wipes or various other personal care items such as facial tissue, bathroom tissue or feminine care products, or may be incorporated into lotions or soaps which may be applied directly to the skin. The antimicrobial formulations of the present invention have been found to have surprisingly high activity against numerous bacteria and other microorganisms.

74 Claims, 4 Drawing Sheets

Solid line = Sample Formulation #5 (Mono/Dialkyl Phosphate)
Circle = Sample Formulation #7 (Citric Acid/Malic Acid/Mono/Dialkyl Phosphate)
Square = Sample Formulation #4 (Sodium Dodecyl Sulfate)
Triangle = Sample Formulation #6 (Citric Acid/Malic Acid/Sodium Dodecyl Sulfate)

U.S. PATENT DOCUMENTS

| Patent No. | | Date | Inventor |
|---|---|---|---|
| 4,481,243 | A | 11/1984 | Allen |
| 4,493,782 | A | 1/1985 | Williamson |
| 4,504,409 | A | 3/1985 | Tsutsumi et al. |
| 4,513,051 | A | 4/1985 | Lavash |
| 4,707,292 | A | 11/1987 | Sano et al. |
| 4,738,847 | A | 4/1988 | Rothe et al. |
| 4,753,749 | A | 6/1988 | McIntosh |
| 4,764,418 | A | 8/1988 | Kuenn et al. |
| 4,772,501 | A | 9/1988 | Johnson et al. |
| 4,824,689 | A | 4/1989 | Kuenn et al. |
| 4,828,912 | A | 5/1989 | Hossain et al. |
| 4,830,764 | A | 5/1989 | Wiedemann |
| 4,836,949 | A | 6/1989 | Klajnscek |
| 4,897,304 | A | 1/1990 | Hossain et al. |
| 4,912,245 | A | 3/1990 | Girardeau et al. |
| 4,931,201 | A | 6/1990 | Julemont |
| 4,943,350 | A | 7/1990 | Bogart et al. |
| 4,968,450 | A | 11/1990 | Kamegai et al. |
| 4,975,217 | A | 12/1990 | Brown-Skrobot et al. |
| 5,015,471 | A | 5/1991 | Birtwistle et al. |
| 5,049,440 | A | 9/1991 | Bornhoeft, III et al. |
| 5,071,585 | A | 12/1991 | Matsunaga et al. |
| 5,078,991 | A | 1/1992 | Birtwistle et al. |
| 5,085,854 | A | 2/1992 | Fukuda et al. |
| 5,093,112 | A | 3/1992 | Birtwistle et al. |
| 5,124,077 | A | 6/1992 | Kajihara et al. |
| 5,141,803 | A | 8/1992 | Pregozen |
| 5,334,387 | A | 8/1994 | Haugk |
| 5,419,908 | A | 5/1995 | Richter et al. |
| 5,436,008 | A | 7/1995 | Richter et al. |
| 5,480,633 | A | 1/1996 | Simion et al. |
| 5,525,345 | A | 6/1996 | Warner et al. |
| 5,525,346 | A | 6/1996 | Hartung et al. |
| 5,525,645 | A | 6/1996 | Ohkawa et al. |
| 5,550,274 | A | 8/1996 | Reierson |
| 5,554,781 | A | 9/1996 | Reierson |
| 5,700,842 | A | 12/1997 | Cole |
| 5,726,206 | A | 3/1998 | Oppong et al. |
| 5,830,487 | A | 11/1998 | Klofta et al. |
| 5,888,524 | A | 3/1999 | Cole |
| 5,905,062 | A * | 5/1999 | Elliott et al. ................ 510/124 |
| 5,919,471 | A | 7/1999 | Saferstein et al. |
| 6,071,961 | A | 6/2000 | Wider |
| 6,183,757 | B1 | 2/2001 | Beerse et al. |
| 6,183,763 | B1 | 2/2001 | Beerse et al. |
| 6,210,695 | B1 * | 4/2001 | Beerse et al. ................ 424/404 |

* cited by examiner

Solid line = Sample Formulation #5 (Mono/Dialkyl Phosphate)
Circle = Sample Formulation#7 (Citric Acid/Malic Acid/Mono/Dialkyl Phosphate)
Square = Sample Formulation #4 (Sodium Dodecyl Sulfate)
Triangle = Sample Formulation #6 (Citric Acid/Malic Acid/Sodium Dodecyl Sulfate)

SOLID LINE = SAMPLE FORMULATION #5 (MONO/DIALKYL PHOSPHATE)
CIRCLE = SAMPLE FORMULATION #7 (CITRIC ACID/MALIC ACID/MONO/DIALKYL PHOSPHATE)
SQUARE = SAMPLE FORMULATION #4 (SODIUM DODECYL SULFATE)
TRIANGLE = SAMPLE FORMULATION #6 (CITRIC ACID/MALIC ACID/SODIUM DODECYL SULFATE)

ANTIMICROBIAL FORMULATIONS

BACKGROUND OF THE INVENTION

The present invention relates to antimicrobial formulations. More specifically, the present invention relates to antimicrobial formulations which are highly effective against a broad range of microorganisms such as bacteria, fungi, yeasts, molds, protozoan, and viruses while substantially less irritating to the skin than previous formulations. The antimicrobial formulations of the present invention can be applied directly to the skin or can be applied to a variety of substances or carriers such as cellulosic webs, nonwoven structures, and textile-based materials, and are particularly useful in products such as facial and bath tissues, wet wipes, diapers, incontinence products, feminine care products, and wound management products.

Today, many consumers are demanding that personal health care products such as wet wipes, diapers, etc. have the ability to not only provide their intended function, but also eliminate to a large extent problem microorganisms, such as rhinoviruses, *Escherichia coli, Staphylococcus aureus,* and *Staphylococcus epidermidis,* for example, while not harming the consumer's health. To meet this demand, antimicrobial agents have been incorporated into a wide range of consumer products, such as wet wipes, to combat both transient and resident bacteria on skin. Antimicrobial-containing products are currently marketed in many forms such as lotions, deodorant soaps, hard surface cleaners, wet wipes, and surgical disinfectants.

Many products that contain antimicrobial agents, however, are harsh or irritating to the skin due to the nature of the chemicals utilized to provide the antimicrobial effect. For example, some hard surface cleaners and surgical disinfectants utilize high levels of alcohol and/or surfactants which have been repeatedly shown to dry out and irritate skin tissues. Other wet wipes currently available utilize harsh cationic surfactants without the addition of acids. Although the surfactant is capable of penetrating and killing many types of bacteria, it is very irritating and harsh to the skin.

Many antimicrobial-containing products utilize an organic acid in combination with an anionic or cationic surfactant as antimicrobial agents. Although some organic acids can safely be utilized in products to control microorganisms without the presence of surfactants, most products incorporating only an organic acid have a low efficacy against bacteria and fungi unless used at very high concentrations. At very high concentrations, these acids can make the ultimate product uneconomical and can even raise skin irritation concerns.

Both anionic and cationic surfactants have, for some time, been known to impart certain benefits to antimicrobial formulations and compositions. Under certain conditions, surfactants exhibit high antimicrobial activity against a broad range of bacteria and other microbes. Although not completely understood, it appears that the surfactants are highly effective in disrupting or disorganizing the outer structure of the microbes allowing direct access into the microbes by other components. As mentioned earlier, the addition of surfactants to antimicrobial formulations is not, however, completely free from problems as many surfactants can be highly irritating to skin.

As such, a need continues to exist for antimicrobial formulations which can be utilized in various products such as wet wipes and facial tissue. Ideally, the antimicrobial formulations and products containing the formulations would gently clean and deodorize the skin while significantly reducing the amount of active microbial agents, while at the same time not drying out or irritating the skin.

SUMMARY OF THE INVENTION

The present invention provides an antimicrobial formulation, a method of using the antimicrobial formulation, and products incorporating an antimicrobial formulation. The antimicrobial formulation of the present invention is highly effective against numerous bacteria, fungi, yeasts, molds, protozoan and viruses yet is gentle to the skin of the user. It has been discovered that when one or more proton donating agents such as organic or inorganic acids are combined with an alkyl phosphate anionic surfactant comprised at least partially of a mono alkyl phosphate, numerous microorganisms are inactivated. Further, the antimicrobial formulations of the present invention are essentially free from an antimicrobial active. A suitable liquid carrier such as water or a woven or non woven substrate is easily used in combination with the antimicrobial formulations of the present invention to inactivate numerous microorganisms. Notwithstanding their high antimicrobial activity, the formulations and products of the present invention have been found to be substantially non-irritating to the skin of the user. Such a combination of highly effective antimicrobial formulations without skin irritation is greatly needed. The present invention can be used to produce products which may be applied directly to the skin such as soaps, lotions or wet-wipes containing the antimicrobial formulations. Alternatively, the present invention can be used to produce products such as bath or facial tissues containing the antimicrobial formulations.

Briefly, therefore, the present invention is directed to a wet wipe comprising a fibrous sheet material and an antimicrobial cleansing solution. The solution is essentially free of an antimicrobial active and comprises a proton donating agent and an alkyl phosphate anionic surfactant which includes a mono alkyl phosphate.

The invention is further directed to a wet wipe comprising a fibrous sheet material and an antimicrobial cleansing solution. The solution is essentially free of an antimicrobial active and comprises a carboxylic acid and an alkyl phosphate anionic surfactant which includes a mono alkyl phosphate. The carboxylic acid comprises from about 0.01 weight percent to about 10 weight percent of the total weight of the solution and the alkyl phosphate anionic surfactant comprises from about 0.01 weight percent to about 10 weight percent of the total weight of the solution.

The invention is further directed to a wet wipe comprising a fibrous sheet material and an antimicrobial cleansing solution. The solution is essentially free of an antimicrobial active and comprises a carboxylic acid and an alkyl phosphate anionic surfactant which includes a mono alkyl phosphate. The antimicrobial cleansing solution has a pH of from about 2 to about 7.

The invention is further directed to a wet wipe comprising a fibrous sheet material and an antimicrobial cleansing solution. The solution comprises a carboxylic acid and an alkyl phosphate anionic surfactant which includes a mono alkyl phosphate, and has a pH of from about 2 to about 3.

The invention is further directed to an antimicrobial formulation for direct application to human skin. The formulation is essentially free of an antimicrobial active and comprises a proton donating agent and an alkyl phosphate anionic surfactant which includes a mono alkyl phosphate.

The invention is further directed to an antimicrobial formulation for direct application to human skin. The formulation is essentially free of an antimicrobial active and comprises a proton donating agent and an alkyl phosphate anionic surfactant which includes a mono alkyl phosphate. The solution has a pH of from about 2 to about 7.

The invention is further directed to an antimicrobial formulation for direct application to human skin. The formulation comprises a proton donating agent and an alkyl phosphate anionic surfactant which includes a mono alkyl phosphate. The solution has a pH of from about 2 to about 3.

The invention is further directed to a product comprising a substrate and an antimicrobial solution. The solution is essentially free of an antimicrobial agent and is comprised of at least about 2 percent of the total dry weight of the substrate of a proton donating agent and from about 0.05 weight percent to about 5 weight percent of the total dry weight of the substrate of an alkyl phosphate anionic surfactant which includes a mono alkyl phosphate.

The invention is further directed to a product comprising a substrate and an antimicrobial solution. The solution is essentially free of an antimicrobial active an is comprised of a proton donating agent and an alkyl phosphate anionic surfactant which includes a mono alkyl phosphate.

Other objects and features of this invention will be in part apparent and in part pointed out hereinafter.

BRIEF DESCRIPTION OF THE DRAWINGS

Corresponding reference characters indicate corresponding parts throughout the drawings.

DEFINITIONS

Figure 1:
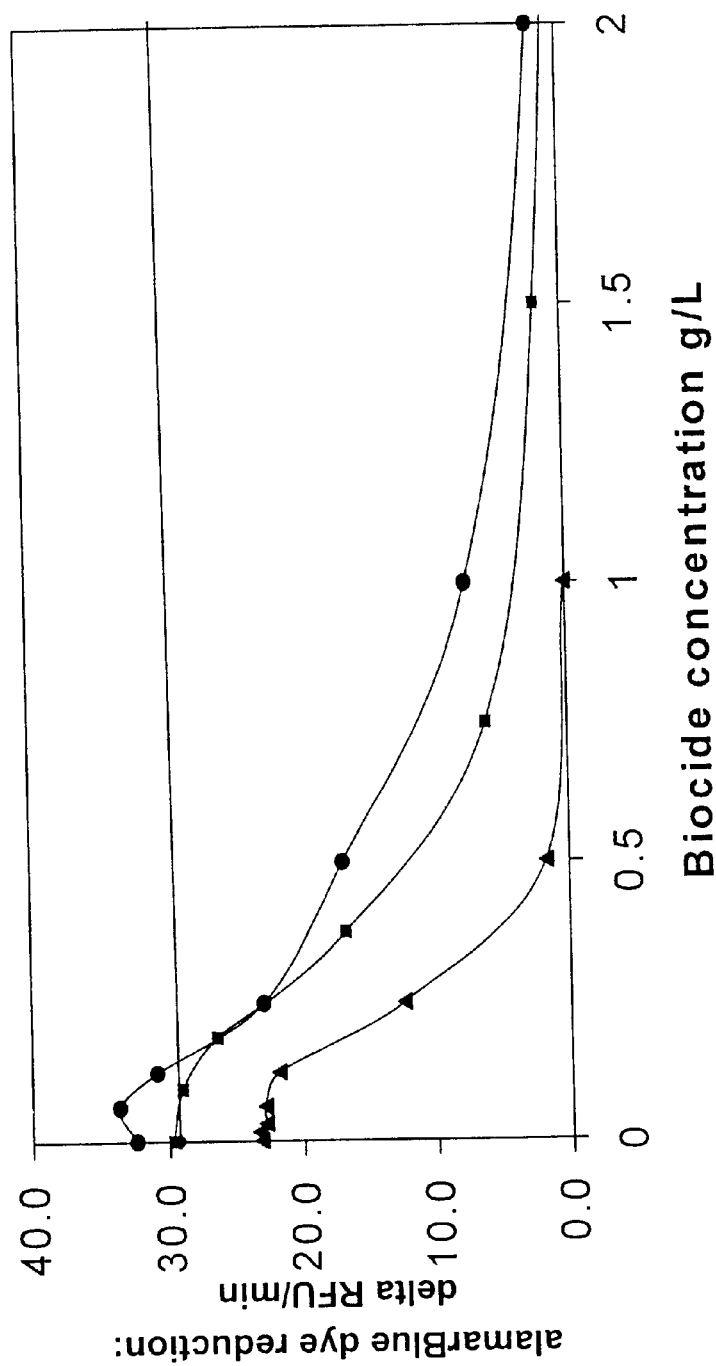
FIG. 1 is a graph showing $IC_{50}$ data of certain sample formulations against *Staphylococcus aureus*.

Within the context of this specification, each term or phrase below will include, but not be limited to, the following meaning or meanings:

(a) "Bonded" refers to the joining, adhering, connecting, attaching, or the like, of two elements. Two elements will be considered to be bonded together when they are bonded directly to one another or indirectly to one another, such as when each is directly bonded to intermediate elements.

(b) "Film" refers to a thermoplastic film made using a film extrusion and/or foaming process, such as a cast film or blown film extrusion process. The term includes apertured films, slit films, and other porous films which constitute liquid transfer films, as well as films which do not transfer liquid.

(c) "Layer" when used in the singular can have the dual meaning of a single element or a plurality of elements.

(d) "Meltblown" refers to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than about 0.6 denier, and are generally self bonding when deposited onto a collecting surface. Meltblown fibers used in the present invention are preferably substantially continuous in length.

(e) "Nonwoven" refers to materials and webs of material which are formed without the aid of a textile weaving or knitting process.

(f) "Polymeric" includes, but is not limited to, homopolymers, copolymers, such as for example, block, graft, random and alternating copolymers, terpolymers, etc. and blends and modifications thereof. Furthermore, unless otherwise specifically limited, the term "polymeric" shall include all possible geometrical configurations of the material. These configurations include, but are not limited to, isotactic, syndiotactic and atactic symmetries.

(g) "Thermoplastic" describes a material that softens when exposed to heat and which substantially returns to a nonsoftened condition when cooled to room temperature.

DETAILED DESCRIPTION OF THE PREFERRED EMBODIMENTS

In accordance with the present invention, it has been discovered that highly effective antimicrobial formulations, which may be applied directly to the skin or incorporated into a substrate such as a woven or non-woven material, are formed when a proton donating agent, such as an organic or inorganic acid, is combined with an alkyl phosphate anionic surfactant which is comprised at least partially of a mono alkyl phosphate. Surprisingly, the antimicrobial formulations of the present invention do not require the addition of an antimicrobial active such as Triclosan® to be highly effective against bacteria, fungi, yeasts, molds, protozoan and viruses.

The antimicrobial formulations of the present invention comprise at least one proton donating agent along with one or more alkyl phosphate anionic surfactants. The one or more alkyl phosphate anionic surfactants are comprised, at least partially, of a mono alkyl phosphate. Although the proton donating agent may be an inorganic acid, it is generally a water soluble carboxylic acid having the following structure (I):

$$R\text{—COOH} \qquad (I)$$

wherein R may be lower alkyl, substituted lower alkyl, hydroxy lower alkyl, such as ($HOCH_2$—), carboxy lower alkyl, such as ($HOOC$—$CH_2CH_2$—), carboxy, hydroxy lower alkyl, such as ($HOOCCH_2CHOH$—), carboxy halo lower alkyl, such as ($HOOCCH_2CHBr$—), carboxy dihydroxy lower alkyl, such as ($HOOC$—$CHOH$—$CHOH$—), dicarboxy hydroxy lower alkyl, such as shown in structure (II):

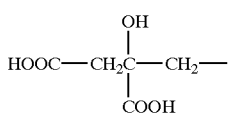

lower alkenyl, carboxy lower alkenyl, such as (HOOCCH=CH—), dicarboxy lower alkenyl, such as shown in structure (III)

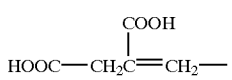

phenyl, such as $C_6H_5$, and substituted phenyl, such as hydroxy phenyl. As used herein, the term "lower" refers to an acid wherein R contains one to six carbon atoms. As used herein, the term "substituted" indicates that one or more hydrogen atoms are substituted by halogen atoms, hydroxyl groups, amino groups, thiol groups, nitro groups, cyano groups, etc.

More specifically, the following acids may be utilized in the formulations of the present invention: acetic acid, dehydroacetic acid, propionic acid, lactic acid, benzoic acid, parahydroxybenzoic acid, ascorbic acid, isoascorbic acid, citric acid, sorbic acid, formic acid, phosphoric acid, malic acid, tartaric acid, adipic acid, succinic acid, caprilic acid, glutaric acid, salicylic acid, boric acid, monohalogenacetic acid, dicarbonic acid, and fumaric acid. Also within the scope of the present invention are salts and esters of the acids described herein. Combinations and mixtures of the acids, acid esters, or acid salts described herein are also within the scope of the present invention. A preferred combination of acids for use in the formulations of the present invention include malic acid and citric acid.

The surfactant component of the antimicrobial formulations of the present invention is a alkyl phosphate anionic surfactant which includes from about 50 weight percent to about 100 weight percent, desirably from about 80 weight percent to about 100 weight percent, based on the total weight of the alkyl phosphate anionic surfactant of a mono alkyl phosphate having the general structure as shown in (IV):

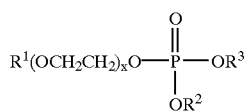

and from about 0 weight percent to about 50 weight percent, desirably from about 0 weight percent to about 20 weight percent, based on the total weight of the alkyl phosphate anionic surfactant of dialkyl phosphate having the general structure as shown in (V):

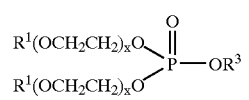

wherein $R^1$ is a saturated or unsaturated straight chain or branched alkyl group having from about 8 to about 22 carbon atoms. Desirably, $R^1$ has from about 10 to about 18 carbon atoms. X is a number from 0 to about 20, desirably from 0 to about 8, and most desirably from 0 to about 3. $R^2$ and $R^3$ are hydrogen, an alkali metal such as sodium, potassium, lithium, rubidium and cesium, ammonium, or an alkanol amine, such as dimethylmonoethanolamine, methyldiethanolamine, trimethylamine, triethylamine, dibutylamine, butyldimethylamine, monoethanolamine, diethanolamine, triethanolamine, isopropyldimethylamine, and isopropylethanolamine.

Suitable mono alkyl phosphate anionic surfactants and methods of making the same for use in the present invention are described in U.S. Pat. No. 4,139,485, U.S. Pat. No. 5,124,077, U.S. Pat. No. 5,550,274, U.S. Pat. No. 5,554,781, and EPO Application No. 0 675 076, the disclosures of which are hereby incorporated by reference. Suitable mono alkyl phosphate surfactants for use in the present invention include, for example, sodium mono lauryl phosphate, potassium mono lauryl phosphate, diethanolamine mono lauryl phosphate, triethanolamine mono lauryl phosphate, sodium mono coco phosphate, potassium mono coco phosphate, triethanolamine mono coco phosphate, sodium mono capric phosphate, potassium mono capric phosphate, triethanolamine mono capric phosphate, and the like as well as combinations and mixtures thereof.

The antimicrobial formulations of the present invention which contain a proton donating agent and an alkyl phosphate anionic surfactant, which is partially comprised of a mono alkyl phosphate, are highly effective against a wide range of microbes, yet are essentially free of an antimicrobial active. Typically, antimicrobial formulations effective against a wide range of microbes contain, in addition to a proton donating agent and a surfactant, at least one antimicrobial active which is used to improve the microbiocidal activity of the formulation and hence the efficacy of the antimicrobial formulation. As used herein, "essentially free of an antimicrobial active" means that the formulation preferably does not contain any antimicrobial active, or that the formulation contains only a trace amount of an antimicrobial active which does not significantly improve or significantly affect the properties of the formulation. Although the exact amount of antibacterial active used in antimicrobial compositions varies depending upon the particular active utilized, typically from about 0.1% to about 0.25% by weight of an antimicrobial active, based on the total weight of the antimicrobial formulation, is added to antimicrobial formulations. Common antimicrobial actives include, for example, Triclosan®, Triclocarban®, Octopirox®, PCMX, ZPT, natural essential oils and their key ingredients, and mixtures or combinations thereof. A preferred antimicrobial active is Triclosan®.

Although antimicrobial actives are commonly utilized in antimicrobial formulations, the antimicrobial formulations of the present invention do not require such antimicrobial actives. It has been found that when combined with an alkyl phosphate anionic surfactant partially comprised of a mono alkyl phosphate, the proton donating agents of the present invention are highly effective against microbes and do not require an antimicrobial active, and the resulting formulation as a whole is extremely mild to the skin. Without the need for an antimicrobial active, the antimicrobial formulations of the present invention are also highly cost effective.

In one embodiment, the formulations of the present invention can be incorporated into a wet wipe, hand wipe, face wipe, cosmetic wipe, household wipe, industrial wipe and the like having improved antimicrobial activity while being gentle to the skin. Materials suitable for the substrate of the wet wipe are well known to those skilled in the art, and are typically made from a fibrous sheet material which may be either woven or nonwoven. For example, the wet wipes incorporating the antimicrobial formulations of the present invention may include nonwoven fibrous sheet materials which include meltblown, coform, air-laid, bonded-carded web materials, hydroentangled materials, and combinations thereof. Such materials can be comprised of synthetic or natural fibers, or a combination thereof. Typically, wet wipes define a basis weight of from about 25 to about 120 grams per square meter and desirably from about 40 to about 90 grams per square meter.

In a particular embodiment, the wet wipes incorporating the antimicrobial formulations of the present invention comprise a coform basesheet of polymeric microfibers and cellulosic fibers having a basis weight of from about 60 to about 80 grams per square meter and desirably about 75 grams per square meter. Such coform basesheets are manufactured generally as described in U.S. Pat. No. 4,100,324, which is incorporated by reference. Typically, such coform basesheets comprise a gas-formed matrix of thermoplastic polymeric meltblown microfibers, such as, for example, polypropylene microfibers, and cellulosic fibers, such as, for example, wood pulp fibers.

The relative percentages of the polymeric microfibers and cellulosic fibers in the coform basesheet can vary over a wide range depending upon the desired characteristics of the wet wipes. For example, the coform basesheet may comprise from about 20 to about 100 weight percent, desirably from about 20 to about 60 weight percent, and more desirably from about 30 to about 40 weight percent of the polymeric microfibers based on the dry weight of the coform basesheet being used to provide the wet wipes.

Alternatively, the wet wipes incorporating the antimicrobial formulations of the present invention can comprise a composite which includes multiple layers of materials. For example, the wet wipes may include a three layer composite which includes an elastomeric film or meltblown layer between two coform layers as described above. In such a configuration, the coform layers may define a basis weight of from about 15 to about 30 grams per square meter and the elastomeric layer may include a film material such as a polyethylene metallocene film.

As previously mentioned, the wet wipes contain an antimicrobial formulation which is absorbed into the wet wipes. The amount of solution contained within each wet wipe may vary depending upon the type of material being used to provide the wet wipe, the type of solution being used, the type of container being used to store the wet wipes, and the desired end use of the wet wipes. Generally, each wet wipe can contain from about 150 to about 600 weight percent and desirably from about 250 to about 450 weight percent solution based on the dry weight of the wipe for improved wiping. In a particular aspect, wherein the wet wipes are made from a coform material comprising from about 30 to about 40 weight percent polymeric microfibers based on the dry weight of the wipe, the amount of solution contained within the wet wipe is from about 300 to about 400 weight percent and desirably about 330 weight percent based on the dry weight of the wet wipe. If the amount of solution is less than the above-identified range, the wet wipe may be too dry and may not adequately perform. If the amount of solution is greater than the above-identified range, the wet wipe may be oversaturated and soggy and the solution may pool in the bottom of the container holding the wet wipes.

The antimicrobial solution incorporated into the wet wipes should contain an amount of proton donating agent and alkyl phosphate sufficient to provide antimicrobial activity without being strongly irritating to the skin. A suitable amount of proton donating agent such as, for example, citric acid, is from about 0.01 weight percent to about 10 weight percent, more desirably from about 0.5 weight percent to about 7 weight percent based on the total weight of the solution. A suitable amount of alkyl phosphate anionic surfactant is from about 0.01 weight percent to about 10 weight percent, more desirably from about 2 weight percent to about 7 weight percent based on the total weight of the solution. The alkyl phosphate component of the antimicrobial formulation is comprised of from about 50 weight percent to about 100 weight percent, more desirably from about 80 weight percent to about 100 weight percent of a mono alkyl phosphate and from about 0 weight percent to about 50 weight percent, more desirably from about 0 weight percent to about 20 weight percent of a dialkyl phosphate. A preferred solution for incorporation into a wet wipe is a combination of citric and malic acids with an alkyl phosphate anionic surfactant comprised of 88% mono alkyl phosphate and 12% dialkyl phosphate.

The antimicrobial solution of the present invention which is incorporated into the wet wipes typically has a pH from about 2 to about 7, more desirably from about 2 to about 5, more desirably from about 2 to about 3, and most desirably from about 2 to about 2.5. This pH range allows the antimicrobial solution of the present invention to be utilized with a high degree of antimicrobial efficacy without being strongly irritating to the skin of the user. The antimicrobial formulation of the present invention can be formulated at such low pHs and still not be strongly irritating to the skin because in combination with a proton donating agent the mono/dialkyl phosphate surfactants are extremely gentle on the skin.

The antimicrobial solution of the present invention which is incorporated into the wet wipes may also optionally contain a variety of other components which may assist in providing the desired wiping and antimicrobial properties. For example, the components may include water, emollients, other surfactants, preservatives, chelating agents, pH buffers, fragrances, antimicrobial actives, or combinations or mixtures thereof. The solution may also contain lotions and/or medicaments. To provide reduced skin irritation, the solution desirably includes at least about 80 weight percent water and more desirably at least about 90 percent water based on the total weight of the solution.

In another embodiment of the present invention, the formulations can be incorporated into products to be directly applied to the skin. Such products may include hand, body and face lotions as well as various types of soaps. The antimicrobial lotion or soaps should contain an amount of proton donating agent and alkyl phosphate anionic surfactant sufficient to provide antimicrobial activity without being strongly irritating to the skin. A suitable amount of proton donating agent for incorporation into lotions is from about 0.1 weight percent to about 10 weight percent, desirably from about 2 weight percent to about 7 weight percent of the total volume of the lotion. A suitable amount of alkyl phosphate anionic surfactant for incorporation into lotions is from about 0.1 volume percent to about 10 volume percent, desirably from about 0.5 volume percent to about 7 volume percent of the total volume of the lotion. The alkyl phosphate component of the antimicrobial formulation is comprised of from about 50 weight percent to about 100 weight percent, more desirably from about 80 weight percent to about 100 weight percent of a mono alkyl phosphate and from about 0 weight percent to about 50 weight percent, more desirably from about 0 weight percent to about 20 weight percent of a dialkyl phosphate.

For soaps, a suitable amount of proton donating agent is from about 0.1 weight percent to about 10 weight percent, desirably from about 2 weight percent to about 7 weight percent of the total volume of the lotion. A suitable amount of alkyl phosphate anionic surfactant is from about 0.1 volume percent to about 60 volume percent, desirably from about 2 volume percent to about 55 volume percent of the total volume of the lotion. The alkyl phosphate component of the antimicrobial formulation is comprised of from about 50 weight percent to about 100 weight percent, more desirably from about 80 weight percent to about 100 weight percent of a mono alkyl phosphate and from about 0 weight percent to about 50 weight percent, more desirably from about 0 weight percent to about 20 weight percent of a dialkyl phosphate.

When incorporated into products which may be applied directly to the skin such as lotions and soaps, the resulting pH of the lotions or soap is typically from about 2 to about 7, more desirably from about 2 to about 5, more desirably from about 2 to about 3, and most desirably from about 2 to about 2.5. This pH range allows the antimicrobial formulation to be utilized with a high degree of antimicrobial efficacy without being irritating to the skin.

The antimicrobial soaps and lotions of the present invention may also optionally contain a variety of other components which may assist in providing the desired cleaning and antimicrobial properties. For example, the soaps or lotions may also contain an alcohol such as ethyl alcohol, isopropyl alcohol, propyl alcohol, or mixtures of ethyl and isopropyl alcohols. Also, the lotions and soaps may contain water, emollients, other surfactants, preservatives, chelating agents, pH buffers, fragrances, antimicrobial actives, or combinations or mixtures thereof. Typically, the lotions and soaps will contain a high percentage of water to reduce the possibility of skin irritation.

In another embodiment, the antimicrobial formulations of the present invention incorporating a one or more proton donating agents and an alkyl phosphate anionic surfactant can be incorporated into a cellulosic web substrate such as facial tissue, bathroom tissue, feminine care product, hand towels, surgical drapes, gowns, bedsheets, pillowcases and the like. In this embodiment, the substrate will typically contain at least about 2 weight percent, based on the dry weight of the substrate, of a proton donating agent and from about 0.05 to about 5 weight percent, based on the dry weight of the substrate, of an alkyl phosphate anionic surfactant. The alkyl phosphate component of the antimicrobial formulation is comprised of from about 50 weight percent to about 100 weight percent, more desirably from about 80 weight percent to about 100 weight percent of a mono alkyl phosphate and from about 0 weight percent to about 50 weight percent, more desirably from about 0 weight percent to about 20 weight percent of a dialkyl phosphate.

The addition of the proton donating agent and alkyl phosphate anionic surfactant to the substrate is preferably performed using a liquid application treater such as a DAHLGREN® LAS. When the proton donating agent and alkyl phosphate anionic surfactant of the present invention are incorporated into a substrate such as a facial tissue and the like, the liquid application composition containing the proton donating agent and alkyl phosphate anionic surfactant preferably have a pH from about 2 to about 7, more desirably more desirably from about 2 to about 5, more desirably from about 2 to about 3, and most desirably from about 2 to about 2.5.

The present invention is illustrated by the following examples which are merely for the purpose of illustration and is not to be regarded as limiting the scope of the invention or manner in which it may be practiced.

EXAMPLE 1

In this Example, the antimicrobial efficacy (in terms of $IC_{50}$ data) of several different formulations against *Staphylococcus aureus, Staphylococcus epidermidis,* and *Escherichia coli* was evaluated. The formulations tested comprised a formulation based upon the present invention as well as several other formulations comprised of various organic acids and/or surfactants, as well as surfactants alone.

Microorganism Preparation: Lyophilized cultures of *Escherichia coli* (ATCC 8739), *Staphylococcus aureus* (ATCC 6538), and *Staphylococcus epidermidis* (ATCC 12,228) were obtained from the American Type Culture Collection (ATCC) (Rockville, Md.). All three cultures were reconstituted according to ATCC specifications. Aliquots (0.5 mL) of reconstituted 24 hour broth growth were frozen and held at −80° C. until needed. Working cultures were prepared weekly by streaking a loop of frozen culture onto tryptic soy agar plates (TSA) (Becton Dickinson Microbiology Systems, Cockeysville, Md.) and then incubating overnight at 37° C. After incubation, the cultures were held at 4° C. for not more than about 5 days.

One day prior to testing, a fresh TSA plate was prepared with a sterile swab to achieve a lawn of growth and incubated at 37° C. for about 24 hours. On the day of testing, the 24 hour lawn of growth was harvested with a sterile cotton swab and suspended to a density of $1\times10^9$ cells/mL in phosphate buffered water (PBW) (Aid-Pack Division of Nutramax Products, Gloucester, Mass.). Cell concentrations were determined in triplicate by taking optical density readings of a sample (200 microliters) with a ThermoMax microplate reader spectrophotometer (Molecular Devices) at 650 nm. From a standard curve the appropriate volume of the PBW containing the cells was determined to prepare $1.1\times10^9$ CFU/mL in the PBW. Exact cell numbers were confirmed by spread plating on TSA and incubating at 37° C.

Sample Formulation Preparation: In this Example, seven sample formulations were tested for antimicrobial efficacy. The active ingredients for the seven sample formulations were as follows: 1) Citric Acid; 2) Malic Acid; 3) Citric Acid/Malic Acid; 4) Sodium Dodecyl Sulfate; 5) Mono/Dialkyl Phosphate; 6) Citric Acid/Malic Acid/Sodium Dodecyl Sulfate; and 7) Citric Acid/Malic Acid/Mono/Dialky Phosphate.

The Citric Acid sample formulation (#1) was prepared as follows: 25 grams of anhydrous citric acid (Baker, Phillipsburgh, N.J.) was added to 1000 mL of Milli-Q water and dissolved. This resulted in a 25 g/L solution of citric acid.

The Malic Acid sample formulation (#2) was prepared as follows: 25 grams of anhydrous malic acid (Aldrich, St. Louis, Mo.) was added to 1000 mL of Milli-Q water and dissolved. This resulted in a 25 g/L solution of malic acid.

The Citric Acid/Malic Acid (1:1) sample formulation (#3) was prepared as follows: 25 grams of anhydrous citric acid (Baker, Phillipsburgh, N.J.) and 25 grams of anhydrous malic acid (Aldrich, St. Louis, Mo.) was added to 1000 mL of Milli-Q water and dissolved. This resulted in a 50 g/L solution of citric acid and malic acid (1:1 ratio, by weight).

The Sodium Dodecyl Sulfate sample formulation (#4) was prepared as follows: 96 grams of sodium dodecyl sulfate was added to 1000 mL of Milli-Q water and dissolved. This resulted in a 96 g/L solution of sodium dodecyl sulfate.

The Mono/Dialky Phosphate sample formulation (#5) was prepared as follows: A sample containing 20% actives of potassium laureth phosphate and potassium dilaureth phosphate was obtained from Rhodia (New Jersey). The sample's 20% actives were comprised of 88% potassium laureth phosphate and 12% potassium dilaureth phosphate. 500 mL of the 20% actives compound was introduced into 1000 mL of water to produce a 10% active (100 g/L) solution.

The Citric Acid/Malic Acid/Sodium Dodecyl Sulfate sample formulation (#6) was prepared as follows: 32.8 grams of anhydrous citric acid (Baker, Phillipsburgh, N.J.), 15.0 grams of anhydrous malic acid (Aldrich, St. Louis, Mo.), and 5.0 grams of sodium dodecyl sulfate (Aldrich, St. Louis, Mo.) were added to 500 mL of Milli-Q water. This produced a 10.5% actives solution, with the ratio of citric acid to malic acid to sodium dodecyl sulfate being about 6.6:3:1.

The Citric Acid/Malic Acid/Mono/Dialkyl Phosphate sample formulation (#7) was prepared as follows: 32.8 grams of anhydrous citric acid (Baker, Phillipsburgh, N.J.), 15.0 grams of anhydrous malic acid (Aldrich, St. Louis, Mo.), and 25.0 grams of a 20% actives solution of Mono/Dialkyl Phosphate were added to 500 mL of Milli-Q water. The 20% actives Mono/Dialkyl Phosphate solution was comprised of 88% potassium laureth phosphate and 12% potassium dilaureth phosphate. This produced a 10.5% actives solution, with the ratio of citric acid to malic acid to sodium dodecyl sulfate being about 6.6:3:1.

Assay Protocol: To all wells of a Microflour®2 96 well microtiter plate (8 Rows by 12 Columns) (Dynex Technologies, Chantilly, Va.) was added 25 microliters of filtered, sterilized water (Millipore Continental Water Systems, Bedford Mass.). After the water was added to the wells, 25 microliters of sample formulation was added to the first row (Row A) across all 12 columns with a multichannel pipetor and aspirated 3 times to thoroughly mix the sample formulation and water combination. After mixing, 25 microliters was transferred from each well in Row A to its corresponding well in Row B to produce a new 50 microliter mixture of sample formulation and water having one half the concentration of sample formulation as that of Row A. The Row B mixtures were aspirated 3 times to thoroughly mix the sample formulation and water combination. These serial dilutions continued down the Rows until reaching Row G (for a total of 6 dilutions from the original plates in Row A). After thorough mixing of Row G well contents, 25 microliters of each well in Row G (a total of 12) was discarded to produce a Row G having 12 columns each containing 25 microliters. This procedure produced 7 Rows of varying concentrations of sample formulation, each Row having twelve columns, and each column having the same concentration of sample formulation.

After serial dilution, bacterial cells were introduced into the wells. In columns 1, 2, and 3 of each Row, 25 microliters (about $2.75 \times 10^7$ cells) of *Staphylococcus aureus* as prepared above was introduced and mixed. In columns 4, 5, and 6 of each Row, 25 microliters (about $2.75 \times 10^7$ cells) of *Staphylococcus epidermidis* as prepared above was introduced and mixed. In columns 7, 8, and 9 of each Row, 25 microliters (about $2.75 \times 10^7$ cells) of *Escherichia coli* as prepared above was introduced and mixed.

The sample formulations as prepared above were appropriately diluted (if necessary) prior to the introduction of the sample formulations into Row A. The dilutions were made such that, after the sample formulation was introduced into Row A, and after the cells were introduced into Row A (i.e., after reducing the initial concentration of the sample formulation by 50% two times), the initial concentrations were as follows:

| Sample Formulation | S. aureus | S. epipdermidis | E. Coli |
|---|---|---|---|
| Citric Acid | 6.25 g/L | 6.25 g/L | 6.25 g/L |
| Malic Acid | 6.25 g/L | 6.25 g/L | 6.25 g/L |
| Citric Acid/Malic Acid | 50 g/L | 3.13 g/L | 100 g/L |
| Sodium Dodecyl Sulfate | 12 g/L | 12 g/L | 96 g/L |
| Alkyl Phosphate | 100 g/L | 100 g/L | 100 g/L |
| Citrate/Malate/SDS | 1 g/L | 1 g/L | 20 g/L |
| Citrate/Malate/AP | 4 g/L | 4 g/L | 8 g/L |

After the addition of the cells, incubation proceeded (5 minutes) at room temperature. After the incubation period, a 1.6 M phosphate buffer (50 microliters) was added to all wells to neutralize the biocide. Then, 3×Letheen broth (50 microliters) (Difco Laboratories, Detroit, Mich.) and Alamar Blue (25 microliters at room temperature) (AccuMed International, Westlake, Ohio) were added to each well.

A positive control was also utilized in the experiment. The positive control consisted of adding sterile Milli-Q water to the wells in place of sample formulation. The positive control wells were thereafter treated identically to the other test wells.

A negative control was also utilized in the experiment. The negative control, which contained a biocidal concentration known to inhibit cell viability, was a 6.6:3:1 (weight) solution of citric acid, malic acid and sodium dodecyl sulfate. After dilution, the final biocide concentration was 6.6 g/L.

Fluorescence Measurements: Fluorescence of Alamar Blue was measured kinetically with an Ascent Fluoroskan Fluorometer (Labsystems Oy, Helsinki, Finland) for about 45 minutes after addition of Alamar Blue. The samples were held at a temperature of about 37° C. during fluorescence measurements. Measurements were conducted with an excitation wavelength filter of 544 nanometers and an emission wavelength of 590 nanometers. Data gathered during the final 30 minutes of fluorescence were used to determine the maximum rate change per well.

Table 1 presents the $IC_{50}$ data for the samples described above. As used herein, $IC_{50}$ is the amount of sample formulation (reported in the g/L) required for a 50% inhibition of Alamar Blue reduction. The reduction for the acid only sample formulation appears to be additive as the 1:1 ratio of citric acid to malic acid exhibited activity similar to that of the same concentration of malic acid alone.

TABLE 1

Biocidal Activities of Test Solutions Reported as the 50% Inhibitory Concentration ($IC_{50}$) in g/L

| Biocide # | S. aureus | S. epidermidis | E. Coil |
|---|---|---|---|
| #1 | 2.2 | 0.71 | >6.3 |
| #2 | 1.3 | 0.24 | 6 |
| #3 | 1.3 | 0.21 | 17.4 |
| #4 | 0.48 | 0.95 | 79.5 |
| #5 | >100 | >100 | >100 |

TABLE 1-continued

Biocidal Activities of Test Solutions Reported as the 50% Inhibitory Concentration ($IC_{50}$) in g/L

| Biocide # | S. aureus | S. epidermidis | E. Coil |
|---|---|---|---|
| #6 | 0.25 | 0.15 | 1.6 |
| #7 | 0.52 | 0.3 | 6.5 |

As Table 1 indicates, without the addition of any acid, the mono/dialkyl phosphate displayed no inhibition against any of the test organisms at the highest concentration tested (100 g/L). The anionic surfactant sodium dodecyl sulfate exhibited inhibition against all organisms tested. The $IC_{50}$ values for sodium dodecyl sulfate against both Staphylococcus aureus and Staphylococcus epidermidis were very low at less than 1 g/L. With Escherichia coli, however, it took about 79 g/L to achieve a 50% reduction.

Figure 2:
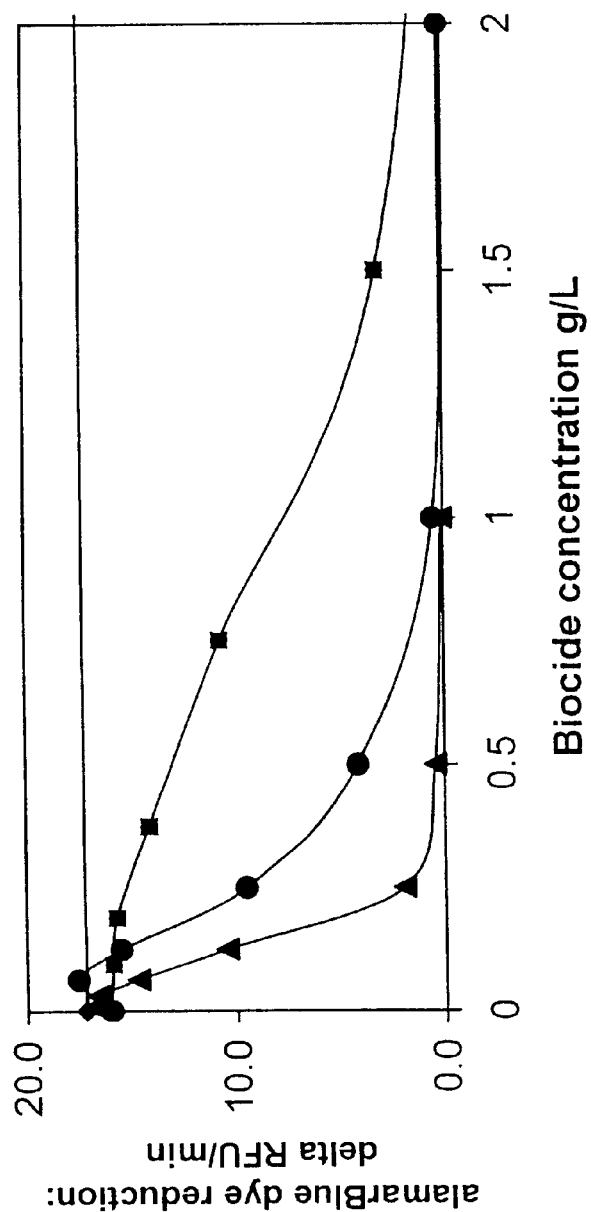
FIG. 2 is a graph showing $IC_{50}$ data of certain sample formulations against *Staphylococcus epidermidis*.
Figure 3:
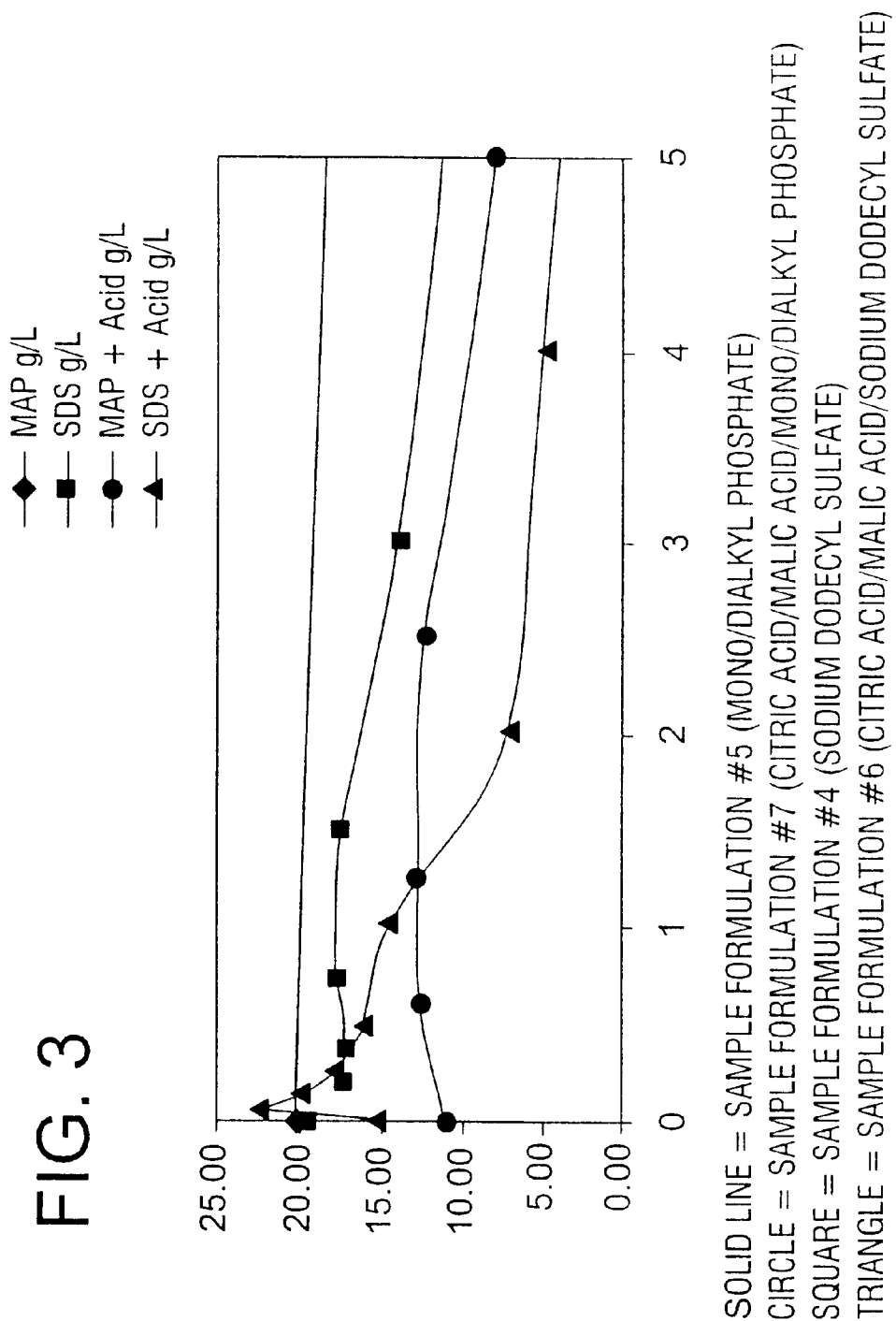
FIG. 3 is a graph showing $IC_{50}$ data of certain sample formulations against *E. coli*.

FIG. 1 graphically shows the $IC_{50}$ data of sample formulations #4, #6, and #7 for Staphylococcus aureus. Although the mono/dialky phosphate biocide did not exhibit significant biocidal activity, as FIG. 1 indicates when the mono/dialky phosphate is combined with citric and malic acids, a significant reduction is achieved. FIGS. 2 and 3 show similar graphic results for biocides against Staphylococcus epidermidis and E. Coli.

EXAMPLE 2

In this Example, corneosurfametry was utilized to evaluate the skin mildness of several different biocides. Skin mildness was evaluated by measuring the damage caused by the biocide on the outer portion of the stratum corneum, and specifically the removal of the lipid component of the stratum corneum.

The following biocide formulations were prepared in triplicate for skin mildness evaluation (percentages are given as w/v, with the solvent being water). The Mono/Dialkyl Phosphate was a solution of 20% actives comprised of 88% potassium laureth sulfate and 12% potassium dilaureth sulfate.

| Formulation | % Surfactant | % Acids |
|---|---|---|
| 1. Mono/Dialkyl Phosphate | 1 | 0 |
| 2. Mono/Dialkyl Phosphate | 0.1 | 0 |
| 3. Mono/Dialkyl Phosphate | 0.01 | 0 |
| 4. Sodium Dodecyl Sulfate | 1 | 0 |
| 5. Sodium Dodecyl Sulfate | 0.1 | 0 |
| 6. Sodium Dodecyl Sulfate | 0.01 | 0 |
| 7. Citric Acid: Malic Acid (6:3) | 0 | 9 |
| 8. Citric Acid: Malic Acid (6:3) | 0 | 0.9 |
| 9. Citric Acid: Malic Acid (6:3) | 0 | 0.09 |
| 10. Citric Acid: Malic Acid: Mono/Dialkyl Phosphate (6:3:1) | 1 | 9 |
| 11. Citric Acid: Malic Acid: Mono/Dialkyl Phosphate (6:3:1) | 0.1 | 0.9 |
| 12. Citric Acid: Malic Acid: Mono/Dialkyl Phosphate (6:3:1) | 0.01 | 0.09 |
| 13. Citric Acid: Malic Acid: Sodium Dodecyl Sulfate (6:3:1) | 1 | 9 |
| 14. Citric Acid: Malic Acid: Sodium Dodecyl Sulfate (6:3:1) | 0.1 | 0.9 |
| 15. Citric Acid: Malic Acid: Sodium Dodecyl Sulfate (6:3:1) | 0.01 | 0.09 |

Human stratum corneum was harvested from adult legs using D-Squame tape biopsies (Cuderm Corporation, Dallas Tex.). Each biopsy harvested consisted of about 7 to 8 pulls from multiple sites on a Caucasian 23 year old female subject's lower leg. After harvesting, the tapes containing the biopsies were soaked in the test biocide (2 mL) in covered six well tissue cultured dishes for 30 minutes at room temperature. Each biocide formulation was tested in triplicate in adjacent wells.

After soaking the tape strips in the biocide, the tape strips were removed and washed for 3 minutes with cold tap water, and dried at room temperature. After drying, the tape strips containing the biopsies were completely immersed in fushin-toluidine blue dye (Polychrome Multiple Stain, PMS: Delasco, Council Bluff, Iowa.) The immersion continued for 3 minutes after which the tape strips were removed and washed for 3 minutes in cold tap water. After washing, the tape strips were allowed to dry completely at room temperature.

The color of the dried samples was measured by color reflectance using a Minolta CR 5000 (Minolta, Osaka, Japan) spectrophotometer. The color measurements recorded the luminance (L*) and chromaticity through Chroma C* described by the equation $(a^{*2}+b^{*2})^{1/2}$. The color differentials between test materials and controls were calculated according to: $[(\Delta L^*)^2+(\Delta C^*)^2]^{1/2}=\Delta E^*ab$. The measurements were taken against controls which were purified water.

Table 2 shows the $\Delta E^*ab$ for each of the formulations tested.

TABLE 2

| Formulation | $\Delta E^*$ ab |
|---|---|
| 1. | 2.05 |
| 2. | 3.21 |
| 3. | 0.27 |
| 4. | 34.41 |
| 5. | 20.76 |
| 6. | 3.36 |
| 7. | 1.17 |
| 8. | 1.15 |
| 9. | 2.79 |
| 10. | 13.9 |
| 11. | 9.23 |
| 12. | 0.52 |
| 13. | 49.28 |
| 14. | 43.62 |
| 15. | 26.48 |

Figure 4:
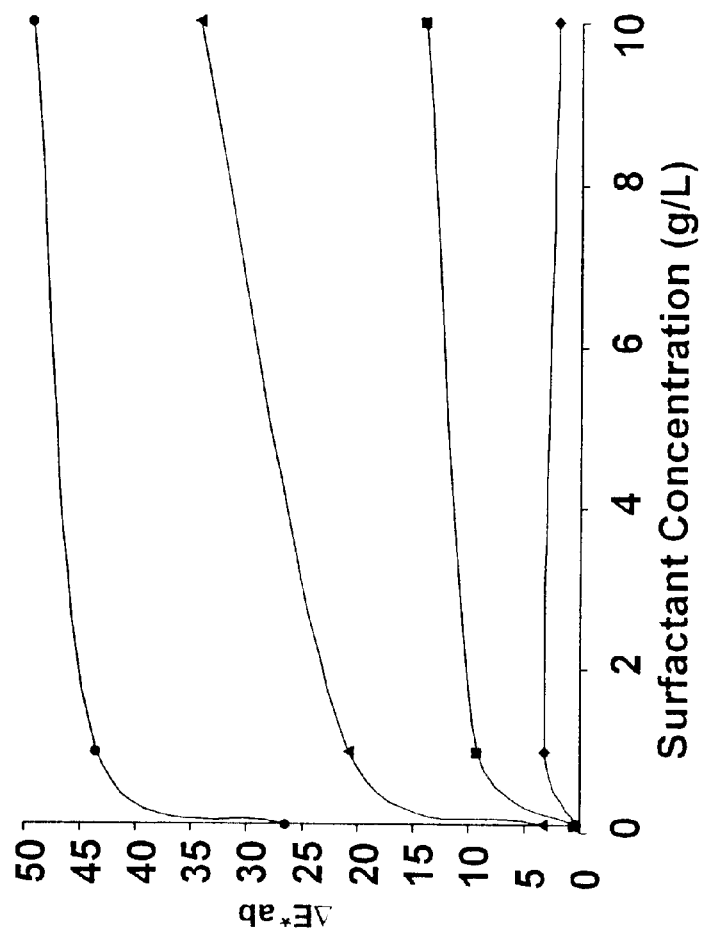
FIG. 4 is a graph showing the effect of surfactant concentration on the amount of dye retained by certain skin biopsies.

The organic acids (citric acid and malic acid) evaluated did not change the dye binding characteristics of the stratum corneum. In contrast, organic acids used in combination with either sodium dodecyl sulfate or mono/dialkyl phosphate increased the skin binding over that of the surfactant alone, as FIG. 4 indicates. This indicates that the acids potentate the destruction of the stratum corneum lipids by surfactants. The effect was more pronounced with sodium dodecyl sulfate than for the mono/dialkyl phosphate. Overall, it can be seen that the mono/dialkyl phosphate had much less impact on the stratum corneum as compared to sodium dodecly sulfate.

In view of the above, it will be seen that the several objects of the invention are achieved. As various changes could be made in the above-described antimicrobial formulations without departing from the scope of the invention, it is intended that all matter contained in the above description be interpreted as illustrative and not in a limiting sense.

What is claimed is:

1. A wet wipe comprising a fibrous sheet material and an antimicrobial cleansing solution effective against bacteria, fungi, yeasts, molds, protozoan and viruses, said solution comprising a proton donating agent and an alkyl phosphate anionic surfactant and being essentially free of an antimicrobial active, the alkyl phosphate anionic surfactant comprising a mono alkyl phosphate having the following structural formula:

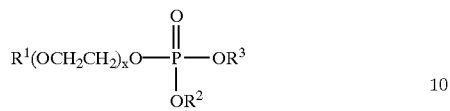

wherein $R^1$ is a saturated or unsaturated straight chain or branched alkyl group having from about 8 to about 22 carbon atoms, x is a number from 0 to about 20, and $R^2$ and $R^3$ are independently selected from hydrogen, an alkali metal, or an alkanol amine.

2. The wet wipe of claim 1 wherein the alkyl phosphate anionic surfactant is comprised of from about 50 weight percent to about 100 weight percent, based on the total weight of the alkyl phosphate anionic surfactant, of the mono alkyl phosphate.

3. The wet wipe of claim 1 wherein the alkyl phosphate anionic surfactant is comprised of from about 80 weight percent to about 100 weight percent, based on the total weight of the alkyl phosphate anionic surfactant, of the mono alkyl phosphate.

4. The wet wipe as set forth in claim 1 wherein the proton donating agent is a carboxylic acid.

5. The wet wipe as set forth in claim 1 wherein the proton donating agent is selected from the group consisting of acetic acid, dehydroacetic acid, propionic acid, lactic acid, benzoic acid, parahydroxybenzoic acid, ascorbic acid, isoascorbic acid, citric acid, sorbic acid, formic acid, phosphoric acid, malic acid, tartaric acid, adipic acid, succinic acid, caprilic acid, glutaric acid, salicylic acid, boric acid, monohalogenacetic acid, dicarbonic acid, fumaric acid, and combinations or mixtures thereof.

6. The wet wipe as set forth in claim 1 wherein the mono alkyl phosphate is selected from the group consisting of sodium mono lauryl phosphate, potassium mono lauryl phosphate, diethanolamine mono lauryl phosphate, triethanolamine mono lauryl phosphate, sodium mono coco phosphate, potassium mono coco phosphate, triethanolamine mono coco phosphate, sodium mono capric phosphate, potassium mono capric phosphate, triethanolamine mono capric phosphate, and combinations and mixtures thereof.

7. The wet wipe as set forth in claim 1 wherein the proton donating agent is a mixture of citric acid and malic acid, and the mono alkyl phosphate is selected from the group consisting of sodium mono lauryl phosphate and potassium mono lauryl phosphate.

8. The wet wipe as set forth in claim 1 wherein x is from 0 to 3.

9. A wet wipe comprising a fibrous sheet material and an antimicrobial cleansing solution effective against bacteria, fungi, yeasts, molds, protozoan and viruses, said solution comprising a carboxylic acid and an alkyl phosphate anionic surfactant and being essentially free of an antimicrobial active, the alkyl phosphate anionic surfactant comprising a mono alkyl phosphate having the following structural formula:

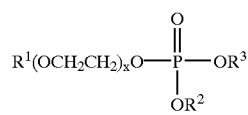

wherein $R^1$ is a saturated or unsaturated straight chain or branched alkyl group having from about 8 to about 22 carbon atoms, x is a number from 0 to about 20, and $R^2$ and $R^3$ are independently selected from hydrogen, an alkali metal, or an alkanol amine, said carboxylic acid comprising from about 0.01 weight percent to about 10 weight percent of the total weight of the solution and said alkyl phosphate anionic surfactant comprising from about 0.01 weight percent to about 10 weight percent of the total weight of the solution.

10. The wet wipe as set forth in claim 9 wherein the alkyl phosphate anionic surfactant is comprised of from about 50 weight percent to about 100 weight percent, based on the total weight of the alkyl phosphate anionic surfactant, of the mono alkyl phosphate.

11. The wet wipe as set forth in claim 9 wherein the alkyl phosphate anionic surfactant is comprised of from about 80 weight percent to about 100 weight percent, based on the total weight of the alkyl phosphate anionic surfactant, of the mono alkyl phosphate.

12. The wet wipe as set forth in claim 9 wherein the carboxylic acid comprises from about 0.5 weight percent to about 7 weight percent of the total weight of the solution and the alkyl phosphate anionic surfactant comprises from about 2 weight percent to about 7 weight percent of the total weight of the solution.

13. The wet wipe as set forth in claim 9 wherein the carboxylic acid is selected from the group consisting of acetic acid, dehydroacetic acid, propionic acid, lactic acid, benzoic acid, parahydroxybenzoic acid, ascorbic acid, isoascorbic acid, citric acid, sorbic acid, formic acid, phosphoric acid, malic acid, tartaric acid, adipic acid, succinic acid, caprilic acid, glutaric acid, salicylic acid, boric acid, monohalogenacetic acid, dicarbonic acid, fumaric acid, and combinations or mixtures thereof.

14. The wet wipe as set forth in claim 9 wherein the mono alkyl phosphate is selected from the group consisting of sodium mono lauryl phosphate, potassium mono lauryl phosphate, diethanolamine mono lauryl phosphate, triethanolamine mono lauryl phosphate, sodium mono coco phosphate, potassium mono coco phosphate, triethanolamine mono coco phosphate, sodium mono capric phosphate, potassium mono capric phosphate, triethanolamine mono capric phosphate, and combinations and mixtures thereof.

15. The wet wipe as set forth in claim 9 wherein the carboxylic acid comprises a mixture of malic acid and citric acid, the mono alkyl phosphate is selected from the group consisting of sodium mono lauryl phosphate and potassium mono lauryl phosphate, the carboxylic acid concentration of the solution is from about 0.5 weight percent to about 7 weight percent of the total weight of the solution and the alkyl phosphate concentration is from about 2 weight percent to about 7 weight percent of the total weight of the solution.

16. The wet wipe as set forth in claim 9 wherein the alkyl phosphate is comprised of from about 80 weight percent to about 100 weight percent, based on the total weight of the alkyl phosphate anionic surfactant, of the mono alkyl phosphate.

17. The wet wipe as set forth in 9 wherein x from 0 to 3.

18. A wet wipe comprising a fibrous sheet material and an antimicrobial cleansing solution effective against bacteria, fungi, yeasts, molds, protozoan and viruses, said solution comprising a carboxylic acid and an alkyl phosphate anionic surfactant and being essentially free of an antimicrobial active, the alkyl phosphate anionic surfactant comprising a mono alkyl phosphate having the following structural formula:

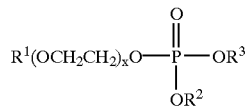

wherein $R^1$ is a saturated or unsaturated straight chain or branched alkyl group having from about 8 to about 22 carbon atoms, x is a number from 0 to about 20, and $R^2$ and $R^3$ are independently selected from hydrogen, an alkali metal, or an alkanol amine, said solution having a pH of from about 2 to about 7.

19. The wet wipe as set forth in claim 18 wherein the solution has a pH of from about 2 to about 5.

20. The wet wipe as set forth in claim 18 wherein the solution has a pH of from about 2 to about 3.

21. The wet wipe as set forth in claim 18 wherein the solution has a pH of from about 2 to about 2.5.

22. The wet wipe as set forth in claim 18 wherein the carboxylic acid is selected from the group consisting of acetic acid, dehydroacetic acid, propionic acid, lactic acid, benzoic acid, parahydroxybenzoic acid, ascorbic acid, isoascorbic acid, citric acid, sorbic acid, formic acid, phosphoric acid, malic acid, tartaric acid, adipic acid, succinic acid, caprilic acid, glutaric acid, salicylic acid, boric acid, monohalogenacetic acid, dicarbonic acid, fumaric acid, and combinations or mixtures thereof.

23. The wet wipe as set forth in claim 18 wherein the mono alkyl phosphate anionic surfactant is selected from the group consisting of sodium mono lauryl phosphate, potassium mono lauryl phosphate, diethanolamine mono lauryl phosphate, triethanolamine mono lauryl phosphate, sodium mono coco phosphate, potassium mono coco phosphate, triethanolamine mono coco phosphate, sodium mono capric phosphate, potassium mono capric phosphate, triethanolamine mono capric phosphate, and combinations and mixtures thereof.

24. The wet wipe as set forth in claim 18 wherein the carboxylic acid comprises from about 0.01 weight percent to about 10 weight percent of the total weight of the solution and the alkyl phosphate anionic surfactant comprises from about 0.01 weight percent to about 10 weight percent of the total weight of the solution.

25. The wet wipe as set forth in claim 18 wherein the carboxylic acid comprises from about 0.5 weight percent to about 7 weight percent of the total weight of the solution and the mono alkyl phosphate anionic surfactant comprises from about 2 weight percent to about 7 weight percent of the total weight of the solution.

26. The wet wipe of claim 18 wherein the alkyl phosphate anionic surfactant is comprised of from about 50 weight percent to about 100 weight percent, based on the total weight of the alkyl phosphate anionic surfactant, of the mono alkyl phosphate.

27. The wet wipe of claim 18 wherein the alkyl phosphate anionic surfactant is comprised of from about 80 weight percent to about 100 weight percent, based on the total weight of the alkyl phosphate anionic surfactant, of the mono alkyl phosphate.

28. The wet wipe as set forth in claim 18 wherein the carboxylic acid is a mixture of citric acid and malic acid and the mono alkyl phosphate anionic surfactant is selected from the group consisting of sodium lauryl mono alkyl phosphate and potassium lauryl mono alkyl phosphate, the citric acid and malic acid comprise from about 0.01 weight percent to about 10 weight percent of the total weight of the solution, the mono alkyl phosphate comprises from about 0.01 weight percent to about 10 weight percent of the total weight of the solution, and the solution has a pH of from about 2 to about 5.

29. The wet wipe as set forth in claim 28 wherein the solution has a pH of from about 2 to about 3.

30. The wet wipe as set forth in claim 28 wherein the solution has a pH of from about 2 to about 2.5.

31. The wet wipe as set forth in claim 28 wherein the citric acid and malic acid comprise from about 0.5 weight percent to about 7 weight percent of the total weight of the solution, the alkyl phosphate comprises from about 2 weight percent to about 7 weight percent of the total weight of the solution, and the solution has a pH of from about 2 to about 5.

32. The wet wipe as set forth in claim 31 wherein the pH of the solution is from about 2 to about 3.

33. The wet wipe as set forth in claim 31 wherein the pH of the solution is from about 2 to about 2.5.

34. The wet wipe as set forth in claim 31 wherein the alkyl phosphate anionic surfactant is comprised of from about 80 weight percent to about 100 weight percent, based on the total weight of the alkyl phosphate anionic surfactant, of the mono alkyl phosphate.

35. A wet wipe comprising a fibrous sheet material and an antimicrobial cleansing solution effective against bacteria, fungi, yeasts, molds, protozoan and viruses, said solution comprising a carboxylic acid and an alkyl phosphate anionic surfactant, the alkyl phosphate anionic surfactant comprising a mono alkyl phosphate having the following structural formula:

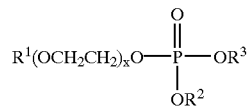

wherein $R^1$ is a saturated or unsaturated straight chain or branched alkyl group having from about 8 to about 22 carbon atoms, x is a number from 0 to about 20, and $R^2$ and $R^3$ are independently selected from hydrogen, an alkali metal, or an alkanol amine, said solution having a pH of from about 2 to about 3.

36. The wet wipe as set forth in claim 35 wherein the solution has a pH of from about 2 to about 2.5.

37. An antimicrobial formulation effective against bacteria, fungi, yeasts, molds, protozoan and viruses suitable for direct application to human skin comprising a proton donating agent and an alkyl phosphate anionic surfactant and being essentially free of an antimicrobial active, the alkyl phosphate anionic surfactant comprising a mono alkyl phosphate having the following structural formula:

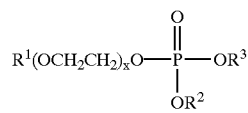

wherein $R^1$ is a saturated or unsaturated straight chain or branched alkyl group having from about 8 to about 22 carbon atoms, x is a number from 0 to about 20, and $R^2$ and $R^3$ are independently selected from hydrogen, an alkali metal, or an alkanol amine.

38. The antimicrobial formulation of claim 37 wherein the alkyl phosphate anionic surfactant is comprised of from about 50 weight percent to about 100 weight percent, based on the total weight of the alkyl phosphate anionic surfactant, of the mono alkyl phosphate.

39. The antimicrobial formulation of claim 37 wherein the alkyl phosphate anionic surfactant is comprised of from about 80 weight percent to about 100 weight percent, based on the total weight of the alkyl phosphate anionic surfactant, of the mono alkyl phosphate.

40. The antimicrobial formulation of claim 37 wherein the proton donating agent is a carboxylic acid selected from the group consisting of acetic acid, dehydroacetic acid, propionic acid, lactic acid, benzoic acid, parahydroxybenzoic acid, ascorbic acid, isoascorbic acid, citric acid, sorbic acid, formic acid, phosphoric acid, malic acid, tartaric acid, adipic acid, succinic acid, caprilic acid, glutaric acid, salicylic acid, boric acid, monohalogenacetic acid, dicarbonic acid, fumaric acid, and combinations or mixtures thereof.

41. The antimicrobial formulation of the claim 37 wherein the mono alkyl phosphate anionic surfactant is selected from the group consisting of sodium mono lauryl phosphate, potassium mono lauryl phosphate, diethanolamine mono lauryl phosphate, triethanolamine mono lauryl phosphate, sodium mono coco phosphate, potassium mono coco phosphate, triethanolamine mono coco phosphate, sodium mono capric phosphate, potassium mono capric phosphate, triethanolamine mono capric phosphate, and combinations and mixtures thereof.

42. The antimicrobial formulation of claim 37 further comprising an alcohol.

43. An antimicrobial formulation effective against bacteria, fungi, yeasts, molds, protozoan and viruses suitable for direct application to human skin comprising a proton donating agent and an alkyl phosphate anionic surfactant and being essentially free of an antimicrobial active, the alkyl phosphate anionic surfactant comprising a mono alkyl phosphate having the following structural formula:

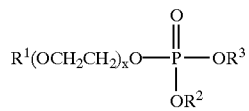

wherein $R^1$ is a saturated or unsaturated straight chain or branched alkyl group having from about 8 to about 22 carbon atoms, x is a number from 0 to about 20, and $R^2$ and $R^3$ are independently selected from hydrogen, an alkali metal, or an alkanol amine, the pH of the formulation being from about 2 to about 7.

44. The antimicrobial formulation of claim 43 wherein the pH of the formulation is from about 2 to about 5.

45. The antimicrobial formulation of claim 43 wherein the pH of the formulation is from about 2 to about 3.

46. The antimicrobial formulation of claim 43 wherein the pH of the formulation is from about 2 to about 2.5.

47. The antimicrobial formulation of claim 43 wherein the alkyl phosphate anionic surfactant is comprised of from about 50 weight percent to about 100 weight percent, based on the total weight of the alkyl phosphate anionic surfactant, of the mono alkyl phosphate.

48. The antimicrobial formulation of claim 43 wherein the alkyl phosphate anionic surfactant is comprised of from about 80 weight percent to about 100 weight percent, based on the total weight of the alkyl phosphate anionic surfactant, of the mono alkyl phosphate.

49. The antimicrobial formulation of claim 43 wherein the formulation contains from about 0.1 weight percent to about 10 weight percent based on the total volume of the formulation and from about 0.1 volume percent to about 10 volume percent of the mono alkyl phosphate anionic surfactant based on the total volume of the formulation.

50. The antimicrobial formulation of claim 43 wherein the formulation contains from about 2 weight percent to about 7 weight percent based on the total volume of the formulation and from about 0.5 volume percent to about 7 volume percent of the mono alkyl phosphate anionic surfactant based on the total volume of the formulation.

51. The antimicrobial formulation of claim 43 wherein the pH of the solution is from about 2 to about 3.

52. The antimicrobial formulation of claim 43 wherein the carboxylic acid is selected from the group consisting of acetic acid, dehydroacetic acid, propionic acid, lactic acid, benzoic acid, parahydroxybenzoic acid, ascorbic acid, isoascorbic acid, citric acid, sorbic acid, formic acid, phosphoric acid, malic acid, tartaric acid, adipic acid, succinic acid, caprilic acid, glutaric acid, salicylic acid, boric acid, monohalogenacetic acid, dicarbonic acid, fumaric acid, and combinations or mixtures thereof.

53. The antimicrobial formulation of claim 43 wherein the mono alkyl phosphate anionic surfactant is selected from the group consisting of sodium mono lauryl phosphate, potassium mono lauryl phosphate, diethanolamine mono lauryl phosphate, triethanolamine mono lauryl phosphate, sodium mono coco phosphate, potassium mono coco phosphate, triethanolamine mono coco phosphate, sodium mono capric phosphate, potassium mono capric phosphate, triethanolamine mono capric phosphate, and combinations and mixtures thereof.

54. The antimicrobial formulation of claim 43 further comprising an alcohol.

55. An antimicrobial formulation effective against bacteria, fungi, yeasts, molds, protozoan and viruses suitable for direct application to human skin comprising a proton donating agent and an alkyl phosphate anionic surfactant, the alkyl phosphate anionic surfactant comprising a mono alkyl phosphate having the following structural formula:

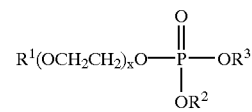

wherein $R^1$ is a saturated or unsaturated straight chain or branched alkyl group having from about 8 to about 22 carbon atoms, x is a number from 0 to about 20, and $R^2$ and $R^3$ are independently selected from hydrogen, an alkali metal, or an alkanol amine, said formulation having a pH of from about 2 to about 3.

56. The antimicrobial formulation of claim 55 wherein the pH is from abut 2 to about 2.5.

57. A product comprising a substrate and an antimicrobial solution effective against bacteria, fungi, yeasts, molds, protozoan and viruses, said solution comprising at least about 2 weight percent of the total dry weight of the substrate of a proton donating agent and from about 0.05 weight percent to about 5 weight percent of the total dry weight of the substrate of an alkyl phosphate anionic surfactant and being essentially free of an antimicrobial active, the alkyl phosphate anionic surfactant comprising a mono alkyl phosphate having the chemical structure:

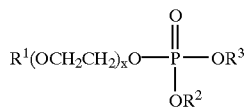

wherein R¹ is a saturated or unsaturated straight chain or branched alkyl group having from about 8 to about 22 carbon atoms, x is a number from 0 to about 20, and R² and R³ are independently selected from hydrogen, an alkali metal, or an alkanol amine.

58. The product of claim 57 wherein the alkyl phosphate anionic surfactant is comprised of from about 50 weight percent to about 100 weight percent, based on the total weight of the alkyl phosphate anionic surfactant, of the mono alkyl phosphate.

59. The product of claim 57 wherein the alkyl phosphate anionic surfactant is comprised of from about 80 weight percent to about 100 weight percent, based on the total weight of the alkyl phosphate anionic surfactant, of the mono alkyl phosphate.

60. The product as set forth in claim 57 wherein the proton donating agent is a carboxylic acid selected from the group consisting of acetic acid, dehydroacetic acid, propionic acid, lactic acid, benzoic acid, parahydroxybenzoic acid, ascorbic acid, isoascorbic acid, citric acid, sorbic acid, formic acid, phosphoric acid, malic acid, tartaric acid, adipic acid, succinic acid, caprilic acid, glutaric acid, salicylic acid, boric acid, monohalogenacetic acid, dicarbonic acid, fumaric acid, and combinations or mixtures thereof.

61. The product as set forth in claim 57 wherein the mono alkyl phosphate anionic surfactant is selected from the group consisting of sodium mono lauryl phosphate, potassium mono lauryl phosphate, diethanolamine mono lauryl phosphate, triethanolamine mono lauryl phosphate, sodium mono coco phosphate, potassium mono coco phosphate, triethanolamine mono coco phosphate, sodium mono capric phosphate, potassium mono capric phosphate, triethanolamine mono capric phosphate, and combinations and mixtures thereof.

62. The product as set forth in claim 57 wherein the proton donating agent is a mixture of citric acid and malic acid and the mono alkyl phosphate anionic surfactant is selected from the group consisting of sodium mono lauryl phosphate and potassium mono lauryl phosphate.

63. The product as set forth in claim 57 wherein the substrate is selected from the group consisting of cellulosic webs and nonwoven webs.

64. A product comprising a substrate and an antimicrobial solution effective against bacteria, fungi, yeasts, molds, protozoan and viruses, said solution comprising a proton donating agent and alkyl phosphate anionic surfactant, and being essentially free of an antimicrobial active, the alkyl phosphate anionic surfactant comprising a mono alkyl phosphate having the chemical structure:

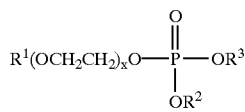

wherein R¹ is a saturated or unsaturated straight chain or branched alkyl group having from about 8 to about 22 carbon atoms, x is a number from 0 to about 20, and R² and R³ are independently selected from hydrogen, an alkali metal, or an alkanol amine.

65. The product as set forth in claim 64 wherein the proton donating agent and alkyl phosphate anionic surfactant are applied to the substrate as a liquid formulation, said liquid formulation having a pH of from about 2 to about 3.

66. The product as set forth in claim 65 wherein the pH of the formulation is from about 2 to about 2.5.

67. A wet wipe comprising a fibrous sheet material and an antimicrobial active-free antimicrobial cleansing solution effective against bacteria, fungi, yeasts, molds, protozoan and viruses, said antimicrobial active-free solution consisting essentially of a proton donating agent, an alkyl phosphate anionic surfactant, and one or more constituents selected from the group consisting of water, emollients, surfactants, preservatives, chelating agents, pH buffers, fragrances, lotions, and medicaments, wherein the alkyl phosphate anionic surfactant comprises a mono alkyl phosphate having the following structural formula:

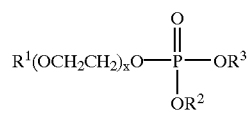

wherein R¹ is a saturated or unsaturated straight chain or branched alkyl group having from about 8 to about 22 carbon atoms, x is a number from 0 to about 20, and R² and R³ are independently selected from hydrogen, an alkali metal, or an alkanol amine.

68. The wet wipe as set forth in claim 67 wherein the solution has a pH of from about 2 to about 5.

69. The wet wipe as set forth in claim 67 wherein the solution has a pH of from about 2 to about 3.

70. The wet wipe as set forth in claim 67 wherein the solution has a pH of from about 2 to about 2.5.

71. An antimicrobial active-free antimicrobial formulation effective against bacteria, fungi, yeasts, molds, protozoan and viruses suitable for direct application to human skin, said antimicrobial active-free antimicrobial formulation consisting essentially of a proton donating agent, an alkyl phosphate anionic surfactant, and one or more constituents selected from the group consisting of water, emollients, surfactants, preservatives, chelating agents, pH buffers, fragrances, lotions, and medicaments, wherein the alkyl phosphate anionic surfactant comprises a mono alkyl phosphate having the following structural formula:

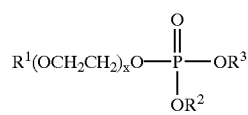

wherein R¹ is a saturated or unsaturated straight chain or branched alkyl group having from about 8 to about 22 carbon atoms, x is a number from 0 to about 20, and R² and R³ are independently selected from hydrogen, an alkali metal, or an alkanol amine.

72. The antimicrobial Formulation as set forth in claim 71 wherein the solution has a pH of from about 2 to about 5.

73. The antimicrobial Formulation as set forth in claim 71 wherein the solution has a pH of from about 2 to about 3.

74. The antimicrobial Formulation as set forth in claim 71 wherein the solution has a pH of from about 2 to about 2.5.

* * * * *

UNITED STATES PATENT AND TRADEMARK OFFICE
CERTIFICATE OF CORRECTION

PATENT NO. : 6,610,314 B2
DATED : August 26, 2003
INVENTOR(S) : Koenig et al.

It is certified that error appears in the above-identified patent and that said Letters Patent is hereby corrected as shown below:

<u>Column 3,</u>
Line 23, "an is comprised" should read -- and is comprised --.

<u>Column 5,</u>
Line 38, "a alkyl" should read -- an alkyl --.

<u>Column 9,</u>
Line 63, "desirably more desirably from" should read -- desirably from --.

<u>Column 11,</u>
Line 34, "Bedford Mass." should read -- Bedford, Mass. --.

<u>Column 12,</u>
Line 8, "S. epipdermidis" should read -- S. epidermidis --.
Line 61, "E. Coil" should read -- E. Coli --.

<u>Column 13,</u>
Line 6, "E. Coil" should read -- E. Coli --.

<u>Column 14,</u>
Line 57, "dodecly" should read -- dodecyl --.

<u>Column 16,</u>
Line 65, "in 9" should read -- in claim 9 --.
Line 65, "x from" should read -- x is from --.

UNITED STATES PATENT AND TRADEMARK OFFICE
CERTIFICATE OF CORRECTION

PATENT NO. : 6,610,314 B2
DATED : August 26, 2003
INVENTOR(S) : Koenig et al.

It is certified that error appears in the above-identified patent and that said Letters Patent is hereby corrected as shown below:

Column 20,
Line 56, "abut 2" should read -- about 2 --.

Signed and Sealed this

Thirtieth Day of March, 2004

JON W. DUDAS
*Acting Director of the United States Patent and Trademark Office*